United States Patent [19]

Steinke

[11] Patent Number: 4,698,264
[45] Date of Patent: Oct. 6, 1987

[54] PARTICULATE COMPOSITION AND PROCESS FOR MAKING SAME

[75] Inventor: James A. Steinke, Jacksonville, Fla.

[73] Assignee: Durkee Industrial Foods, Corp., Iselin, N.J.

[21] Appl. No.: 730,756

[22] Filed: May 3, 1985

Related U.S. Application Data

[63] Continuation-in-part of Ser. No. 403,966, Aug. 2, 1982, abandoned.

[51] Int. Cl.⁴ .................... A23L 1/222; B01J 13/02
[52] U.S. Cl. .................... 428/402.2; 71/100; 71/DIG. 1; 264/4.4; 424/408; 424/469; 424/488; 426/96; 426/97; 426/650; 426/651; 428/402.24; 514/963
[58] Field of Search .................... 426/96, 97, 650, 651; 264/4.4; 428/402.2

[56] References Cited

U.S. PATENT DOCUMENTS

| | | | |
|---|---|---|---|
| 2,809,895 | 10/1957 | Swisher | 426/651 X |
| 3,041,180 | 6/1962 | Swisher | 426/96 |
| 3,495,988 | 2/1970 | Balassa | 428/402.2 X |
| 3,704,137 | 11/1972 | Beck | 426/651 |
| 3,956,507 | 5/1976 | Shoaf et al. | 426/96 |

OTHER PUBLICATIONS

Hawley: The Condensed Chemical Dictionary, 10th ed., 1981, Van Nostrand Reinhold Co.: New York, pp. 185, 936, 937, 949.

Primary Examiner—Richard D. Lovering
Attorney, Agent, or Firm—Richard H. Thomas

[57] ABSTRACT

A solid, water-dispersible, delayed-release particulate composition comprising: a matrix composition, a relatively small amount of an active ingredient insoluble in and uniformly distributed through the matrix composition, the matrix composition comprising: a normally solid, slowly water soluble or slightly water soluble salt selected from the group consisting of alkali metal and calcium phosphates, citrates, tartrates and carbonates, and hydrates thereof, and readily cold water soluble bulking agent.

14 Claims, 1 Drawing Figure

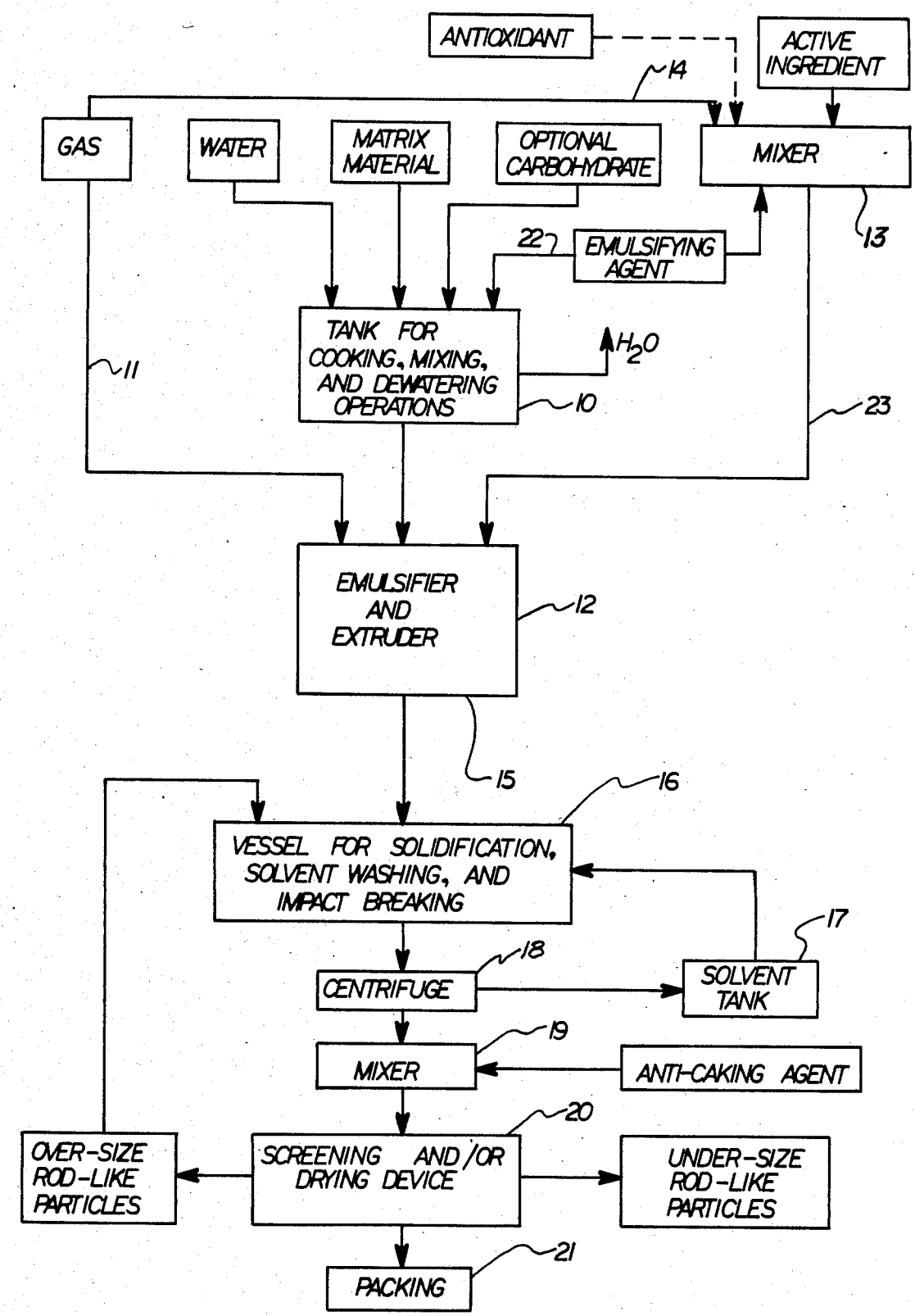

PARTICULATE COMPOSITION AND PROCESS FOR MAKING SAME

This application is a continuation-in-part of prior application Ser. No. 403,966, filed Aug. 2, 1982, now abandoned assigned to assignees' of the present application.

The present invention relates to particulate compositions and process for making the same, and more particularly to such compositions which have entrapped in them an active ingredient such as a flavorant, an odorant, a drug or agricultural chemicals. These compositions are particularly useful in the production of sugar-free chewing gum, sugar-free or low-sugar candy, e.g., breath deodorizers, dentifrices, time-release herbicides, and insecticides, and will be described with respect to the same, although it will be apparent to those skilled in the art that the present invention has many other applications.

BACKGROUND OF THE INVENTION

U.S. Pat. No. 3,704,137 of Nov. 28, 1972 defines certain relatively stable particulate essential oil-rich compositions and a process for preparing the same. In the commercial practice of this prior invention, a melt of sucrose and hydrolyzed cereal solids having a selected, restricted dextrose equivalent is mixed with an essential oil to form an emulsion. The melt is then extruded into cool, agitated isopropanol to produce solidified saccharated particulates entrapping the oil inside them while washing off exposed oil. After drying, the product particulates are usually coated with an anticaking agent. They are stated, in the patent, to be suitable for use in flavoring and/or odorizing beverage powders, pastries, and other ultimate products. Dissolution of the saccharated matrix in water releases the essential oil.

Advantages of the instant invention over this and related prior proposals such as U.S. Pat. No. 3,041,180 include an ability to protect effectively active ingredients for a much wider variety of end-use applications, to make particles free of sucrose and other sugars when desired, and even to control the rate of release of the encapsulated active ingredients to a much greater degree than ever before possible.

BRIEF STATEMENT OF THE INVENTION

Briefly stated, the present invention is in a solid, water dispersible, delayed-release particulate composition comprising: a matrix composition; a relatively small amount of an active ingredient insoluble in and uniformly distributed through the matrix composition; the matrix composition comprising (1) a normally solid, water disintegrable salt selected from the group consisting of alkali metal and calcium phosphates, citrates, tartrates and carbonates, and hydrates thereof; and (2) a cold water soluble bulking agent preferably selected from the group consisting of a partially hydrolyzed cereal solid, having a Dextrose Equivalent (DE) less than about 25 (maltodextrin), a chemically modified food starch, a polysaccharide such as polydextrose, a polyhydric alcohol such as sorbitol, and combinations thereof.

The composition of the present invention is further characterized by the absence of the active ingredient on the exterior surface of the particles.

By the term "water-disintegrable" it is meant that the alkali metal or calcium salt is slowly soluble or slightly soluble in water. Excluded are compounds which are insoluble in water and compounds which are highly soluble in water.

Preferably, the composition of the present invention is prepared by extrusion from a hot cook, such as a solution or dispersion of the matrix ingredients and active ingredient, into a cold alcohol bath at a temperature effective for solidifying the matrix composition. In this regard, a further criteria of the present invention is that the alkali metal or calcium salt be alcohol insoluble.

The proportions of ingredients employed in the present invention depend upon such factors as processing conditions, desired rate of release of active ingredient, and physical properties desired (e.g., hardness and pliability). Broadly, the amount of water disintegrable salt should, at a minimum, be an effective amount to provide delayed release. Generally, the ratio of water disintegrable salt and bulking agent will be in the range of about 35:65 to 65:35.

BRIEF DESCRIPTION OF THE DRAWING

The present invention and advantages thereof will become more apparent from the following specification, with reference to the accompanying drawing, which is a process/flow diagram for a preferred embodiment of the present invention.

DETAILED DESCRIPTION OF THE PRESENT INVENTION

Matrix Composition

As indicated above, the matrix composition of the present invention comprises primarily a water-disintegrable alkali metal or calcium salt and a cold water soluble bulking agent such as a partially hydrolyzed cereal solid (maltodextrin). Alkali metal and calcium salts can be classified as soluble, slightly soluble, and insoluble or nearly insoluble in cold water. If soluble, they can be slowly soluble or dissolved slowly, or rapidly soluble in water. In the present invention, the salt component should be either slightly soluble or slowly soluble in water.

Although not to be bound by theory, it is believed that the presence of a relatively water soluble bulking agent such as the maltodextrin allows water to attack the integrity of the particle, to initiate release of active ingredient, whereas the presence of a less soluble component tends to preserve such integrity a sufficient degree to prolong release.

The function of the salt in the present invention is to provide, in addition to delayed or controlled release, a fused, glassy or hard appearance and texture for the particle. In this respect, the appearance of the products of the present invention, preferably, should be similar to the appearance of particles made in accordance with the teachings of prior U.S. Pat. No. 3,704,137, referred to above, which utilizes a melt of sucrose and hydrolyzed cereal solids, extruded into a cool, agitated isopropanol solvent. The present invention has, as one advantage over the compositions of the U.S. Pat. No. 3,704,137 patent, the advantage that the particles can be non-cariogenic if no sugar is used.

Preferably, the alkali metal or calcium salt employed in the practice of the present invention is neither highly basic nor highly acidic. As mentioned, the salt is an alkali metal or calcium phosphate, citrate, tartrate, carbonate, or hydrate thereof. Specific suitable salts useful in the present invention are listed in the following Table 1:

TABLE 1

| COMPOUND | FORMULA | pH | SOLUBILITY |
|---|---|---|---|
| Sodium hexametaphosphate | $(NaPO_3)_n \cdot NH_2O$ | 7 | soluble, but dissolves slowly |
| Dicalcium phosphate | $CaHPO_4$ | 7.5 | sparingly soluble |
| Tricalcium phosphate | $3Ca_3(PO_4)_2 \cdot Ca(OH)_2$ | | sparingly soluble |
| Sodium ammonium phosphate | $NaNH_4HPO_4$ | 7.8–8.2 | 1 gram in 5 grams water |
| Sodium tripolyphosphate | $Na_5O_{10}P_3$ | — | 1 gram in 5 grams of water |
| Monopotassium phosphate | $K H_2PO_4$ | 4.4 | 1 gram in 5 grams of water |
| Trisodium phosphate | $Na_3PO_4$ | 11.8 | 13 grams in 100 grams water |
| Calcium citrate | — | — | sparingly soluble |
| Calcium tartrate | $C_4H_4CaO_6$ | | sparingly soluble |
| Calcium carbonate | $CaCO_3$ | | sparingly soluble |
| Ammonium carbonate | $(NH_4)_2 CO_3$ | | slowly soluble in water |

All of the above compounds are insoluble or substantially insoluble in alcohol. Preferred compounds are sodium hexametaphosphate, dicalcium phosphate and tricalcium phosphate, being nearly neutral in solution and either sparingly soluble or slowly soluble in water. The solubility data in all of the above is for cold water. Water solubility here means the capability of dissolving in water at room temperature to form a solution of at least about 1 gram per 100 grams of water at ambient temperature. Above a solubility of about 20 grams per 100 grams of water, the composition is deemed to be too water soluble.

Salts such as sodium and potassium tartrates, citrates and carbonates, although useful in the present invention, are better employed in non-food applications.

The second critical ingredient of the matrix composition of the present invention is the bulking agent. A preferred bulking agent is a maltodextrin. Maltodextrins are identified by Chemical Abstract Registry No. 9050-36-6. Reference also may be had to U.S. Pat. No. 3,974,033 to Harjes et al., dated Aug. 10, 1976 and to the prior art discussed therein. The maltodextrins useful herein preferably have a low DE in the range of about 3 to 20, and are marketed as a fine powder. Generally, they are made by first liquifying native starch with an acid or an enzyme to a DE less than about 15 followed by enzymatic conversion, e.g., with bacterial alpha-amylase (notice U.S. Pat. No. 3,849,194 and U.S. Pat. No. RE 30,880). As pointed out in U.S. Pat. No. 3,974,033, maltodextrins are first prepared in syrup form and then spray dried to a moisture content of about 3–5% by weight. These prior art maltodextrin materials, and those prepared from oxidized starch as described in U.S. Pat. No. 3,974,033, are useful herein.

The present invention has also been successfully practiced using a polyhydric alcohol as the bulking agent. A preferred polyhydric alcohol is sorbitol. Mannitol is the only other polyhydric alcohol commercially or readily available, and it is too hygroscopic and provides, as a general rule, a product which is sticky. Sorbitol is marketed as a fine grade powder similar to maltodextrin, and functions in the product and process of the present invention similar to maltodextrin. It is highly water soluble and coacts with the inorganic salt, in the extrusion and solidification steps, to be described, to physically trap the active ingredient. It has a lower molecular weight than maltodextrin, and thus is not as film forming and capable of as high loadings.

Another suitable bulking agent is a chemically modified starch derivative of waxy maize, preferably one which is lipophilic. An example of one such starch is hydrogen, octenylbutanedioate, amylodextrin. The composition has a Chemical Abstract Registry No. 61932-62-5, and is commercially available from National Starch and Chemical Corp. under the trademark "Capsul", and from American Maize Products Co. under the trademark "Amaizo ARD 2326". The composition is described in detail in copending U.S. application Ser. No. 692,486, filed Aug. 2, 1982, assigned to assignee of the present application. This disclosure of Ser. No. 692,486 is incorporated by reference herein. An advantage of this starch compound is that it is very lipophilic and thus, when used, results in significantly higher loadings, when the active ingredient is an oil, such as an essential oil, than otherwise possible.

A fourth possible bulking agent is a polysaccharide such as polydextrose, described in detail in copending U.S. application Ser. No. 730,368, filed May 3, 1985. The disclosure of this application is also incorporated by reference herein.

Polysaccharides are prepared by the thermal condensation polymerization of monosaccharides in the presence of an acid and a polyol. A preferred such polysaccharide is polydextrose prepared from D-glucose with small amounts of sorbitol and citric acid. Maltose can also be polymerized to a polysaccharide. Other food grade acids can be used.

This compound is identified by Chemical Abstracts Registry Number 68424-04-4 and is described in the publication "Chemistry of Foods and Beverages: Recent Developments", copyright 1982, Academic Press, Inc., in the chapter entitled "The Functional Applications of Polydextrose". Reference can also be had to prior U.S. Pat. Nos. 3,766,165 and 3,876,794. This compound is approved for food use (21 CFR 172,841).

In the Academic Press publication, suggested uses include: bulking agent in low calorie foods; formulation aid improving the flowability of a dry mix; humectant and texturizer in formulated food products. Specific food approved uses are baked goods, chewing gum, confections and frostings, dressings for salads, frozen desserts and mixes, gelatins, puddings and candy.

Its use in an extruded product as an encapsulating matrix has not heretofore been suggested.

It is also possible to use combinations of the above ingredients as the bulking agent in the preparation of an encapsulating matrix.

For example, the combination of maltodextrin with sorbitol, with polydextrose, and with Capsul (trademark) has been successfully practiced.

A very useful combination is about 90% maltodextrin to about 10% Capsul, down to 60% maltodextrin and 40% Capsul (based on the weight of the bulking agent), for optimum loading and extrudability. High amounts of the modified starch (Capsul) in the melt prior to extrusion can make too viscous a melt (especially without viscosity controlling agents) and require too high an extrusion pressure to be feasible.

Examples of viscosity controlling agents that can be used are propylene glycol and lecithin.

Generally, sorbitol, because of its strong flavor, would be used in an amount less than about 10% in the formulation, based on total particle weight, so that the balance of the composition would be essentially the inorganic salt and maltodextrin. With some applications, however, the flavor may be desirable and more than 10% could be used.

Above, it was mentioned that the amount of water-disintegrable salt employed should at least be an effective amount to provide delayed release. Also, in the practice of the present invention, the ratio of bulking agent to alkali metal or calcium salt can be varied somewhat so that the end product is more friable or more elastic as needed, the salt providing more friability, the bulking agent, e.g., maltodextrin, in higher proportion providing more elasticity. Again, preferred proportions are 35:65 to 65:35 salt to bulking agent. The proportions preferably should be such that the composition flows in the extrusion step, to be described, as a coherent liquid at a temperature of about 240°–250° F. (115°–121° C.), and that it is ostensibly solidified for handling at ambient temperature, e.g., 70° F.

Active Ingredient

Any active ingredient or agent that will not be damaged materially by the temperatures of melting the matrix, or from contact with the ingredients therein, or which is not fugitive in the process of the present invention, may be employed in the practice of the present invention. This includes such materials as essential oils (citrus essential oils, garlic oil, wintergreen oil, spearmint oil, peppermint oil, lavendar or lavendin oil) whether compounded or extended synthetically or obtained directly from nature, and oleoresins of spices such as pepper. Pharmaceutical agents such as calcium gluconate likewise can be encapsulated by the practice of the present invention, as can pesticides such as methylcarbamate (Sevin) or even somewhat fugitive agents such as acetaldehyde or other materials capable of being absorbed onto or into very finely divided solids such as a starch, charcoal, impalpable materials (alumina, colloidal silica, etc.) or very finely divided polymers.

The proportion of active agent or ingredient to be incorporated in the matrix of the present invention may be varied, depending upon the strength desired in the final product. Generally, the amount of active ingredient will be less than about 25%, based on the weight of the matrix composition. In some end uses, a lower loading of about 5–15%, e.g., 10% may be desirable. The active ingredients useful herein are desirably normally liquid and form a distinct dispersed phase in the hot matrix in the formation of the melt prior to extrusion.

Additional Ingredients

If the active ingredient is oily, it is desirably emulsified in the melt. Emulsifiers are normally used in an amount ranging from about 0.25% to about 5% by weight. Emulsifiers such as mono-diglycerides of stearic or oleic acids, octa-glycerol esters of fatty acids, e.g., octa-glycerol monostearate, polysorbates, alkali metal sulfonates, glyceryl-lacto esters of stearic and oleic acids, and dioctyl sodium sulfo-succinate, are useful for such purpose.

Monosaccharides such as glucose and fructose should not be employed in amounts greater than about 5–6% since they make the product too sticky. While some sucrose, a disaccharide, usually in a minor proportion, is permissible in certain matrices for the instant practice, many end-use applications call for a low sucrose content or the elimination of sucrose entirely. In embodiments such as insecticides, sugars are useful as insect attractants. Similarly, inclusion or elimination of such sucrose or sugar may be desirable with respect to hydrolyzed cereal solids such as corn syrup solids and the like.

In some instances natural gums such as gum arabic, tragacanth gums or gum acacia, dextrins, etc., carboxymethyl cellulose, methyl cellulose, and the like are desirable to form a part of the matrix, along with inorganic salt. Such gums may have emulsifying capabilities which aid in the entrapment of oils, and may also contribute good film forming characteristics. Products containing the gums, at less than about 20%, based on the matrix weight, form less friable rods than the same formula with only maltodextrin. Normally, the gums will not be employed in compositions also having a modified starch in the matrix as the combination creates too viscous a product. Colorants, e.g., approved food colors and/or pigmentation and antioxidants also can be dispersed in the melt if and in the amounts desired. Other inorganic salts can be included in the matrix in addition to the above, in small amounts, up to about 20% based on total salt weight, to modify rate of release or other properties. Examples are potassium chloride which has a solubility of 1 gram in 2.8 ml of water; monoammonium phosphate (solubility 1 gram in 2.5 ml of water); diammonium hydrogen phosphate (solubility 1 gram in 1.7 ml of water); sodium acid pyrophosphate (soluble); tripotassium phosphate (soluble); tetrapotassium pyrophosphate (soluble); and sodium acid pyrophosphate (soluble).

Procedure

In essence, referring to the drawing, a tank 10 is provided, having heating and agitating means, to effect the steps of mixing and cooking. Initially, the matrix ingredients, water and other ingredients such as emulsifying agent and viscosity controlling agent, if desired, are charged into the tank, and the mass is stirred and subjected to heating or cooking, under a vacuum effective to remove water, until the boiling point of the mixture reaches, by way of example, about 104°–116° C. At this point, the cook is terminated and the active ingredient is added in line 23 to the matrix materials in the amount up to about 25 weight percent. Mixing is carried out until complete, still at about the same elevated temperature, since no substantial cooling takes place.

As shown in the drawing, the active ingredient and an emulsifying agent may be premixed in mixer 13, prior to addition to the melt, or the emulsifying agent can be added directly to the melt in line 22.

In the above procedure, the amount of water used initially is a solubilizing amount, sufficient to solubilize the matrix ingredients. During the boiling, the amount is reduced to about 3–12%, for instance about 10%, depending in part upon proportions of ingredients and viscosity desired (for the subsequent extrusion step). The vacuum selected for the boiling or cooking step is dependent in part on the active ingredient to be added.

Cooking at 120° C. would prevent adding a highly volatile active ingredient to the cook solution. A typical vacuum may be about 685 mm Hg.

Use of a higher vacuum permits boiling at a temperature even as low as about 70°–80° C., permitting use of even more volatile active ingredients.

In this regard, use of an alkali metal or calcium salt in the matrix, without sucrose, has the advantage that it permits prolonged cook to a low water content. Sugars exposed to high temperature for a long period of time tend to invert, and invert sugars can give an unsuitable, sticky matrix.

Once the active ingredient is added, the composition is in the form of an emulsion or slurry, depending upon whether the active ingredient is oil based or water based.

The cooking tank 10 is provided with an extrusion cap or spinneret, marked as item 12, preferably isolated from the tank by a valve (not shown). Opening the valve allows the tank contents to move under pressure through the extrusion cap or spinneret into a basket carried in a shallow tray 16 of cold solvent for the active ingredient, such as isopropyl alcohol or ethanol. The extruder has a head provided with a large number of about 1/64" diameter orifices through which the combined mix is forced under 20 to 150 psig air pressure, established by pressure lines 11 and 14. The cold solvent serves two purposes, to remove excess active ingredient from the surface of the extrudate, and to effect solidification of the extruded melt (an example of a solvent temperature effective to solidify the extrudate is about −10° C.). In the tank 16, the extruded rods can be subjected to agitation and comminution to wash off the excess oil, and also to break up the rods into desired lengths, e.g., 1/100" to ¼" long. From the tank, the broken-up rods are separated from a major portion of the liquid solvent by a settling or draining action, and the broken-up rods are then charged into a centrifuge 18 to remove most of the liquid solvent, the solvent being discharged from the centrifuge into a solvent tank 17.

The particulate, rod-like solids from the centrifuge are discharged into a mixer 19, into which is also charged an anticaking agent. The preferred anticaking agent is siliceous material, preferably pyrogenic silica, of a particle size comparable to that desired in the final essential oil composition. The anti-caking agent is incorporated into the melt mix prior to drying and screening (in device 20), but the siliceous material can be added to the liquid solvent prior to extrusion or can be added to the rod-like particles after the centrifuging step. Other anti-caking agents include a silicophosphate, a non-swelling starch, and talc.

The finished product, transferred to packing zone 21, contains an amount of essential oil up to about 25% of oil by weight of the finished product. The product has good keeping properties in that it will not crystallize upon long standing, nor is it subject to substantial deterioration if suitably packaged and protected by antioxidants. The use of about 0.5% to 5% by weight of the final composition of pyrogenic silica powder effectively prevents the rod-like particles of the composition from sticking together upon long standing in a packaged condition and, also, facilitates the transfer of the composition from the packages to the points of actual use of the composition.

The products of this invention have remarkable stability or shelf life, and very low detectable odor in the dry powder state. They dissolve or disintegrate in an aqueous medium slowly or on a time-release basis to free the entrained oil or other active ingredient or ingredients.

In the drawing, the active ingredient is shown being introduced into the melt at the extruder head. An alternative is introducing it into the melt during or near the end of cooking, if it is a less volatile material. Materials of construction for practicing this invention advantageously are corrosion-resistant and readily cleaned. Typically, stainless steel equipment is desirable for these purposes.

The method of preparing the encapsulates of the present invention is analogous to that of U.S. Pat. No. 3,704,137 to Beck.

The following examples show ways in which this invention can be practiced, but are not to be construed as limiting it. In this specification, unless otherwise expressly indicated, all parts are parts by weight, all temperatures are in degees centigrade, and all percentages are weight percentages.

EXAMPLE 1

Reference is again made to the drawing. Agitated vessel 10 is charged with 300 parts of sodium hexametaphosphate, 283 parts of sorbitol, and 450 parts of deliberately added water. This mixture is agitated and heated to remove the water to a level not greater than 8%. This can be accomplished at atmospheric pressure or under vacuum.

As an emulsifying agent, 9.6 parts of octa-glycerol ester of oleic acid (Santone 8-1-0, trademark SCM Corporation) are introduced into mixing tank 13. Mixing tank 13 also contained 66 parts peppermint oil. The emulsifier and peppermint oil were charged through line 23 in addition to the melt delivered there from vessel 10. These components are emulsified to form an extrudable melt that is quite homogeneous. The melt, at 110° C. is forced through spinneret extruder 15, using gas (air) pressure from line 11 to deliver thin (about ½ mm) continuous, viscous strands into vessel 16. This vessel contains a body of agitated isopropanol at −10° C., the isopropanol being supplied from tank 17. The strands are solidified, comminuted, and washed in vessel 16. The resulting comminutate is centrifuged in centrifuge 18 to practical dryness, and the isopropanol-rich filtrate is returned to tank 17. The resulting cleansed particulates are charged to mixer 19 and there coated with an anticaking agent, e.g., pyrogenic silica or any of the other known anticaking agents, e.g., talc, calcium carbonate, etc., if desired using 2 parts of silica per hundred parts of the particles. The particles are screened in screener 20 to separate oversize and undersize material and excess anticaking agent. Product of desired screen size is packed at station 21 into containers for storage. The product is useful as a flavorant material in end use applications required to be low in sugar or sugar free.

EXAMPLE 2

In this example the process is conducted in the same way as that of Example 1 except that 300 parts of dicalcium phosphate ($CaHPO_4$) and 283 parts of maltodextrin (5–20 DE corn syrup solids) are used instead of the sodium hexametaphosphate and the sorbitol. The active ingredient blended into the melt is 66 parts of natural orange essence oil. The product is useful in end use applications in which sucrose cannot be added.

EXAMPLE 3

In this example the process is conducted in essentially the same way as that of Example 1 except that 200 parts of potassium chloride (KCl), 200 parts of tricalcium phosphate ($3Ca_3(PO_4)_2Ca(OH)_2$), and 200 parts of hydrolyzed cereal solids are used instead of the sodium hexametaphosphate and sorbitol in the formulation of the precook mixture. The active ingredient blended into the melt after cooking is 60 parts of the contact insecticide "Sevin" (1-naphthyl-N-methylcarbamate). The "Sevin" is added as a dry powder 10-30 microns in size. The addition of 10-60 parts of an insect attractant such as citral or eugenol can also be added at this point if the intended use of the insecticide is directed at insect species attracted to these compounds. The product obtained (100-500 microns in size) is useful as an insecticide where dusting or drifting associated with small particles needs to be prevented. Material handling is simplified. The addition of tricalcium phosphate provides a controlled release to prolong the effectiveness of the insecticide. Incorporation of an insect attractant such as a di-, tri- or oligosaccharide increases product effectiveness and minimizes amount of insecticide required. Volatilization of the attractant is prevented by the particle formation.

EXAMPLE 4

In this example the process is conducted in essentially the same way as that of Example 3 except that 200 parts of dicalcium phosphate ($CaHPO_4$), 200 parts of maltodextrin (5-20 DE) and 200 parts of sucrose are combined with 450 parts of added water. The resultant mixture is heated, either atmospherically or under vacuum, until its moisture content is less than 8%. The active agent blended into the melt is 60 parts of the insecticide, Malathion (0,0-dimethyldithiophosphate of diethyl mercaptossuccinate, see U.S. Pat. No. 2,578,652). The product is useful as an alternative to liquid Malathion. The unpleasant odor of Malathion in a liquid form is greatly reduced. The product can be applied in combination with fertilizers to minimize application time. The product can be used as a baited insecticide, the sucrose and hydrolyzed cereal solids serving as insect attractants. Mechanism of the release of Malathion in the product is either physical breakdown of the particle or moisture release. Because dicalcium phosphate is relatively insoluble in water, the relative proportion of dicalcium phosphate to the water soluble sucrose and hydrolyzed cereal solids in the product can be used to control the release of Malathion and prolong its effectiveness in the outside environment.

EXAMPLE 5

In this example the process is conducted in essentially the same way as Example 1 except that 200 parts of dicalcium phosphate, 200 parts of mono-ammonium phosphate ($NH_4H_2PO_4$), and 200 parts of hydrolyzed cereal solids are used instead of the sodium hexametaphosphate/sorbitol blend in the formulation of the precook mixture and the active ingredient blended into the melt after cooking is 60 parts of the herbicide, "Sutan" (S-ethyl diisobutylthiocarbamate).

The product produced is useful as 100-500 micron particulate for dry mix application of "Sutan". "Sutan" is currently used in preplant applications and must be incorporated into the soil to reduce losses by volatilization. Photooxidation and volatilization are minimized and the product can be used after the crops have been planted both as a preemergent and postemergent herbicide. Minimum dust when used, controlled release as determined by moisture and dicalcium phosphate levels, and improved stability are primary advantages.

EXAMPLE 6

In this example, 134.2 grams of maltodextrin (46.08%), 142.5 grams of dicalcium phosphate (48.92%) and 14.58 grams of sorbitol (5%) were combined with a sugar-free peppermint essential oil and octaglycerol monooleate emulsifier, and processed as in Example 1. Heating was carried out to a moisture content of about 8.5%. The strands were soft during extrusion but became rigid after being left in isopropal alcohol for about 1 hour. The product is useful as a delayed-release flavor in chewing gum.

EXAMPLE 7

This example is similar to Example 6, producing a sugar-free, cinnamon-flavored particle suitable for chewing gum.

In this example, 2228.89 grams (46.08%) of maltodextrin, 241.85 grams of sorbitol (5%), and 2366.26 grams (48.92) of dicalcium phosphate were added with 2900 millileters of water. The resultant mixture was heated to remove about 97% of the water. At this point, 274 grams of essential oil (cinnamon) and 80 grams of octaglycerol monooleate were added and mixed into the matrix ingredients by agitation for about twenty minutes. The composition was then extruded slowly into isopropanol and dry ice using an orifice plate of 0.033 inches. The strands were slightly discontinuous, but of overall good quality. The moisture content was about 4.8%. The composition is useful as a flavor for chewing gum.

EXAMPLE 8

In this example the same composition and procedures as in Example 6 were employed, except that cooking was carried out for a sufficient period of time to remove 3300 millileters of water (only 2900 millileters added). Following extrusion and centrifuging, the particles were mixed with silica anti-caking agent, then rewashed with isopropanol, centrifuged again, mixed again with anti-caking agent, and then dried for 3 hours.

In the procedure of Example 6, some sticking of particles together was experienced. In the procedure of this example, no sticking together of particles was observed.

What is claimed is:

1. A solid, water-dispersible, delayed-release particulate composition comprising
    a matrix;
    a relatively small amount of an active ingredient insoluble in and uniformly distributed through the matrix;
    the matrix comprising
    (1) a normally solid, slowly water soluble or slightly water soluble and alcohol insoluble salt fusible to a glassy, solid texture selected from the group consisting of alkali metal and calcium phosphates, citrates, tartrates, carbonates, hydrates thereof and combinations thereof; and
    (2) a readily cold water soluble bulking agent selected from the group consisting of maltodextin, a chemically modified food starch, polydextrose, polyhydric alcohol and combinations thereof;

the salt and bulking agent being present in the composition in a matrix forming amount and in the approximate ratio of 35:65 to 65:35 salt to bulking agent;

said particulate composition having a fused, glassy appearance and texture prepared by extrusion of the composition ingredients from a hot aqueous cook into a cold alcohol bath; said particulate composition being substantially free of active ingredient on the external surface thereof.

2. The particulate composition of claim 1 wherein said salt is selected from the group consisting of sodium hexametaphosphate, dicalcium phosphate, tricalcium phosphate, sodium ammonium phosphate, sodium tripolyphosphate, monopotassium phosphate, trisodium phosphate, calcium citrate, calcium tartrate, calcium carbonate, ammonium carbonate, and combinations thereof.

3. The particulate composition of claim 1 wherein said salt is selected from the group consisting of sodium hexametaphosphate, dicalcium phosphate and tricalcium phosphate.

4. The particulate composition of claim 1 further characterized by said particles having a light coating of pulverulent anti-caking agent.

5. The particulate composition of claim 1 wherein said active ingredient is an essential oil.

6. The particulate composition of claim 1 wherein said matrix is substantially sugar-free.

7. The particulate composition of claim 1 further characterised by the presence therein of about 0.25% to about 5% by weight of an emulsifier.

8. The particulate composition of claim 1 prepared by
   (a) forming a hot aqueous cook of the matrix ingredients and carrying out the heating of said cook until a moisture content of less than about 10% is obtained;
   (b) dispersing within such cook said active ingredient;
   (c) extending the cook and active ingredient into a cold alcohol bath at a temperature effective for solidifying the matrix composition; and
   (d) separating the extruded material into finely divided particles.

9. A solid, water-dispersible, delayed-release particulate composition comprising
   a matrix;
   a relatively small amount of an active ingredient insoluble in and uniformly distributed through the matrix;
   the matrix comprising
     (1) a normally solid, slowly water soluble or slightly water soluble and alcohol insoluble salt fusible to a glassy, solid texture, selected from the group consisting of sodium hexametaphosphate, dicalcium phosphate, tricalcium phosphate, sodium ammonium phosphate, sodium tripolyphosphate, monopotassium phosphate, trisodium phosphate, calcium citrate, calcium tartrate, calcium carbonate, ammonium carbonate, and combinations thereof; and
     (2) a readily cold water soluble bulking agent selected from the group consisting of maltodextrin, a chemically modified food starch, polydextrose, a polyhydric alcohol, and combinations thereof;
   the salt and bulking agent being present in the composition in a matrix forming amount and in the approximate ratio of 35:65 to 65:35 salt to bulking agent;
   (3) said particulate composition being prepared by the steps of
     (a) forming a hot aqueous cook of the matrix composition ingredients and carrying out the heating of said cook until a moisture content of less than about 10% is obtained;
     (b) dispersing within such cook said active ingredient;
     (c) extruding the cook and active ingredient into a cold alcohol bath at a temperature effective for solidifying the matrix composition; and
     (d) separating the extruded material into finely divided particles;
   said particulate composition having a fused, glassy appearance and texture and being substantially free of active ingredient on the external surface thereof.

10. The composition of claim 9 wherein said bulking agent is maltodextrin.

11. The composition of claim 9 wherein said bulking agent is sorbitol.

12. A method of preparing a water dispersible, delayed-release particulate composition comprising the steps of
   (a) forming a hot aqueous cook of matrix ingredients and carrying out the heating of said cook until a moisture content of less than about 10% is obtained;
   (b) dispersing within such cook an active ingredient;
   (c) extruding the cook and active ingredient into a cold alcohol bath at a temperature effective for solidifying the matrix; and
   (d) separating the extruded material into finely divided particles,
   said matrix ingredients comprising
     (1) a normally solid, slowly water soluble or slightly water soluble and alcohol insoluble salt fusible to a glassy, solid texture selected from the group consisting of alkali metal and calcium phosphates, citrates, tartrates, carbonates, hydrates thereof, and combinations thereof; and
     (2) a readily cold water soluble bulking agent selected from the group consisting of maltodextrin, a chemically modified food starch, polydextrose, a polyhydric alcohol and combinations thereof;
   the salt and bulking agent being present in the composition in a matrix forming amount and in the approximate ratio of 35:65 to 65:35 salt to bulking agent;
   said matrix having a fused, glassy appearance and texture and being substantially free of active ingredient on the external surface thereof.

13. The method of claim 12 wherein said salt is selected from the group consisting of sodium hexametaphosphate, dicalcium phosphate, tricalcium phosphate, sodium ammonium phosphate, sodium tripolyphosphate, monopotassium phosphate, trisodium phosphate, calcium citrate, calcium tartrate, calcium carbonate, ammonium carbonate, and combinations thereof.

14. The method of claim 12 wherein said salt is selected from the group consisting of sodium hexametaphosphate, dicalcium phosphate and tricalcium phosphate.

* * * * *